(12) United States Patent
Bacon

(10) Patent No.: US 8,734,363 B2
(45) Date of Patent: May 27, 2014

(54) COAXIAL NEEDLE ASSEMBLY

(71) Applicant: Inrad, Inc., Grand Rapids, MI (US)

(72) Inventor: Chad J. Bacon, Coopersville, MI (US)

(73) Assignee: Inrad, Inc., Grand Rapids, MI (US)

( * ) Notice: Subject to any disclaimer, the term of this patent is extended or adjusted under 35 U.S.C. 154(b) by 0 days.

(21) Appl. No.: 13/669,923

(22) Filed: Nov. 6, 2012

(65) Prior Publication Data

US 2013/0060161 A1    Mar. 7, 2013

Related U.S. Application Data

(62) Division of application No. 12/173,181, filed on Jul. 15, 2008, now Pat. No. 8,343,072.

(60) Provisional application No. 60/949,966, filed on Jul. 16, 2007.

(51) Int. Cl.
*A61B 5/00* (2006.01)

(52) U.S. Cl.
USPC .......................................................... 600/567

(58) Field of Classification Search
USPC ............................ 600/564–567; 604/117, 198
See application file for complete search history.

(56) References Cited

U.S. PATENT DOCUMENTS

| | | | |
|---|---|---|---|
| 2,516,492 A * | 7/1950 | Turkel | 600/564 |
| 4,142,517 A | 3/1979 | Contreras Guerrero de Stavropoulos et al. | |
| 4,243,048 A * | 1/1981 | Griffin | 600/564 |
| 5,014,717 A | 5/1991 | Lohrmann | |
| 5,147,380 A * | 9/1992 | Hernandez et al. | 606/207 |
| 5,217,438 A | 6/1993 | Davis et al. | |
| 5,257,632 A | 11/1993 | Turkel et al. | |
| 5,368,046 A | 11/1994 | Scarfone et al. | |
| 5,820,554 A | 10/1998 | Davis et al. | |
| 5,882,344 A | 3/1999 | Stouder, Jr. | |
| 5,916,175 A | 6/1999 | Bauer | |
| 5,951,489 A | 9/1999 | Bauer | |
| 5,954,670 A * | 9/1999 | Baker | 600/567 |
| 6,656,132 B1 | 12/2003 | Ouchi | |
| 6,749,576 B2 | 6/2004 | Bauer | |
| 7,131,951 B2 | 11/2006 | Angel | |
| 7,278,972 B2 * | 10/2007 | Lamoureux et al. | 600/567 |
| 7,309,317 B2 | 12/2007 | Miller et al. | |
| 7,491,189 B2 * | 2/2009 | Sims | 604/117 |
| 7,678,077 B2 * | 3/2010 | Harris et al. | 604/117 |
| 8,088,081 B2 | 1/2012 | Field et al. | |
| 8,197,419 B2 | 6/2012 | Field et al. | |
| 8,202,277 B2 * | 6/2012 | Ryan | 606/107 |
| 2003/0163062 A1 | 8/2003 | Bauer | |
| 2004/0077973 A1 | 4/2004 | Groenke et al. | |
| 2005/0096507 A1 | 5/2005 | Prosek | |
| 2005/0187519 A1 | 8/2005 | Harris et al. | |
| 2005/0267383 A1 | 12/2005 | Groenke et al. | |
| 2006/0030785 A1 | 2/2006 | Field et al. | |

(Continued)

*Primary Examiner* — Max Hindenburg

(74) *Attorney, Agent, or Firm* — McGarry Bair PC

(57) ABSTRACT

An adjustable coaxial needle assembly for placement into a tissue mass prior to a biopsy procedure comprises a guide cannula assembly, a stylet, and a throw calibrator. The stylet is selectively coaxially received by the guide cannula, which is in turn coaxially received by the throw calibrator. The effective length of the guide cannula can be selectively adjusted by moving the throw calibrator relative to the guide cannula to adjust the distance between an open distal end of the guide cannula and a the throw calibrator.

19 Claims, 13 Drawing Sheets

(56) References Cited

U.S. PATENT DOCUMENTS

| | | |
|---|---|---|
| 2006/0200040 A1 | 9/2006 | Weikel, Jr. et al. |
| 2006/0200041 A1 | 9/2006 | Weikel, Jr. et al. |
| 2006/0200042 A1 | 9/2006 | Weikel, Jr. et al. |
| 2008/0139960 A1 | 6/2008 | Tonomura et al. |

* cited by examiner

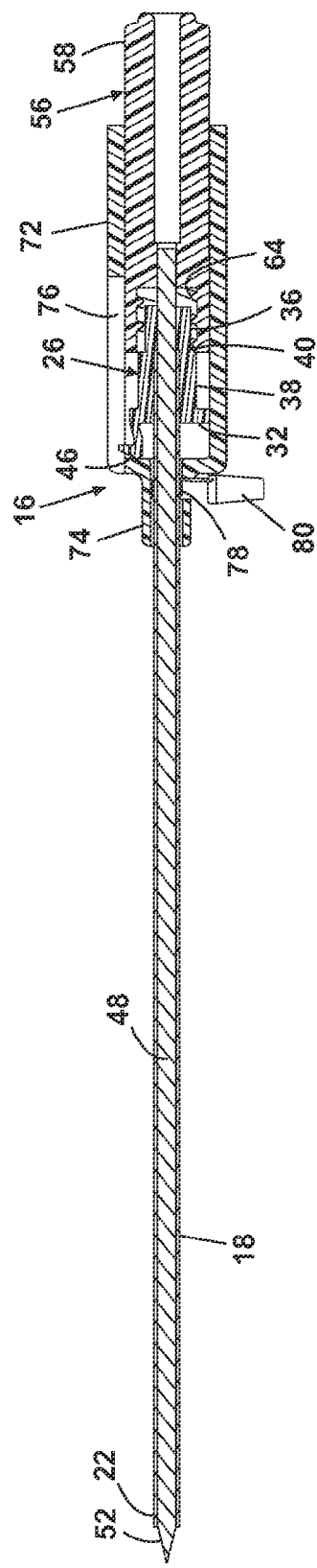
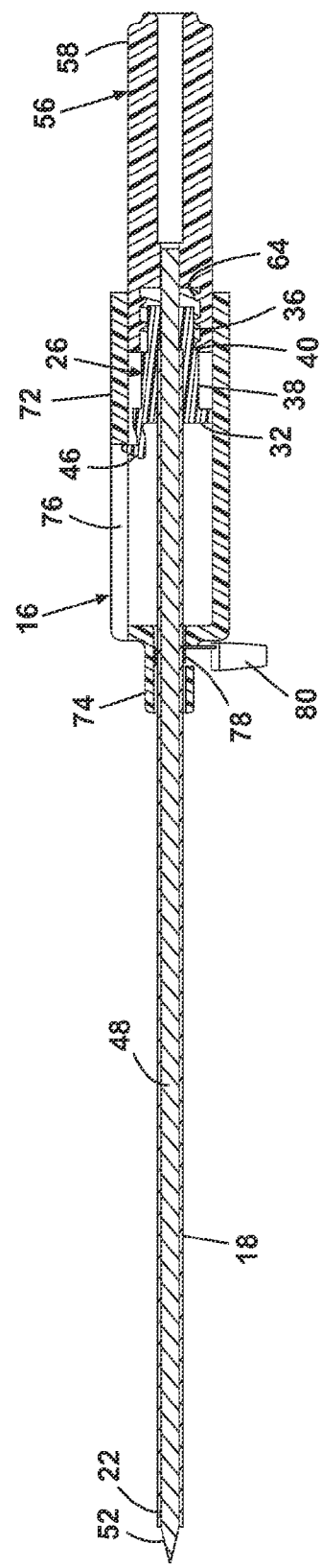
Fig. 6A
Fig. 6B

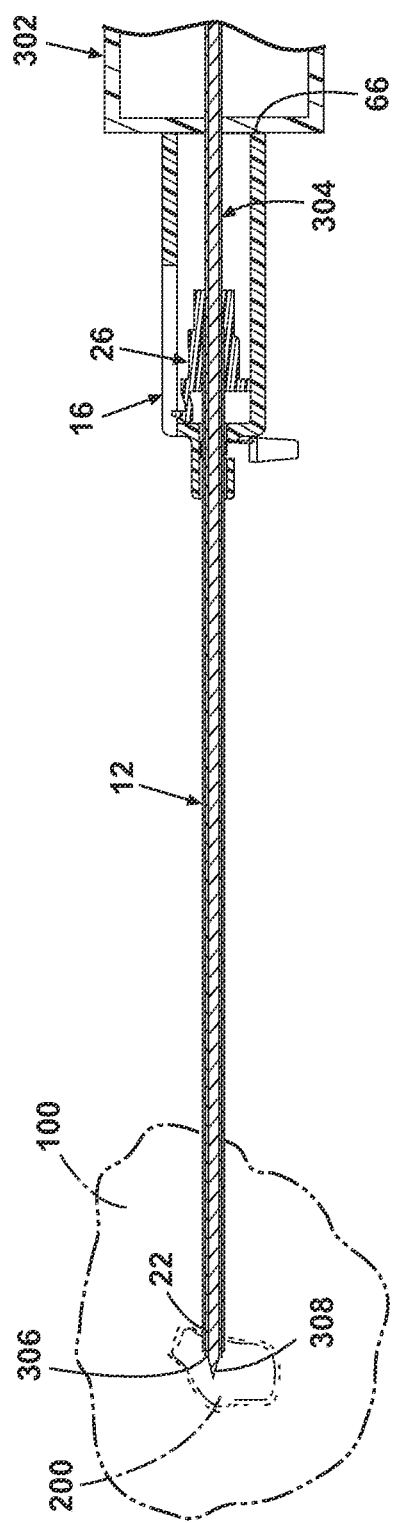

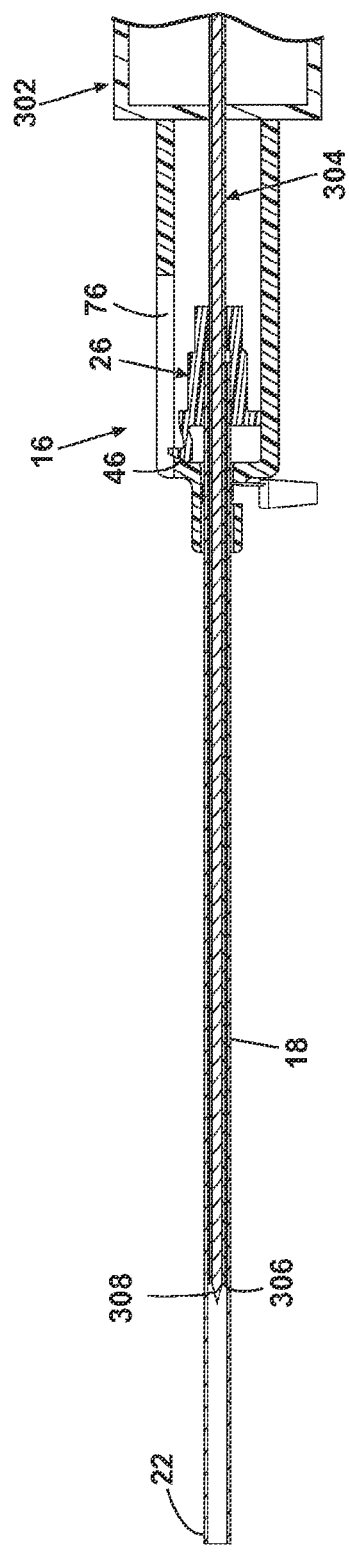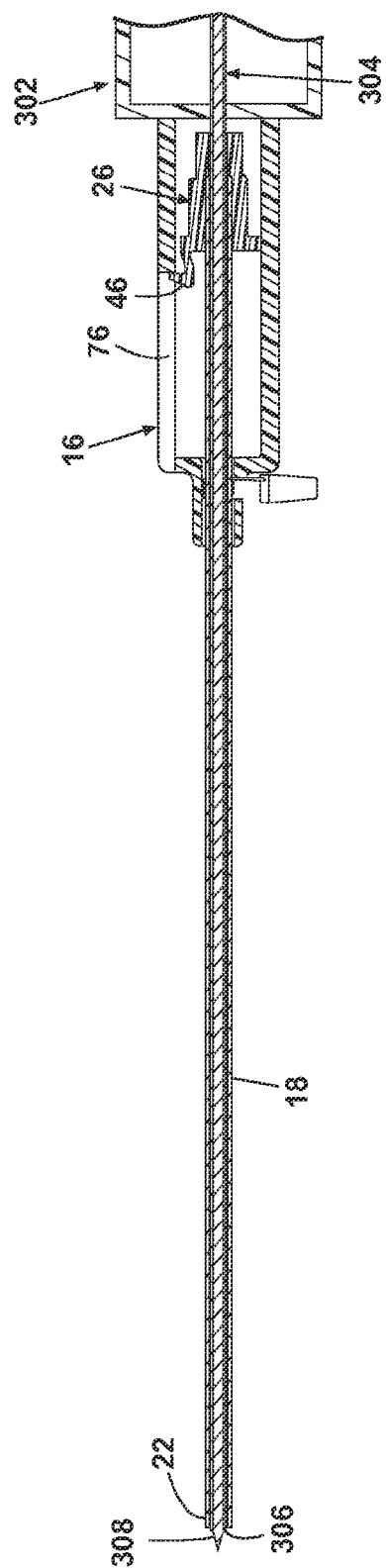
Fig. 9A
Fig. 9B

COAXIAL NEEDLE ASSEMBLY

CROSS-REFERENCE TO RELATED APPLICATION

This application is a divisional of U.S. patent application Ser. No. 12/173,181, filed Jul. 15, 2008, now U.S. Pat. No. 8,343,072, issued Jan. 1, 2013, which claims the benefit of U.S. Provisional Patent Application No. 60/949,966, filed Jul. 16, 2007, both of which are incorporated herein by reference in its entirety.

BACKGROUND OF THE INVENTION

1. Field of the Invention

In one aspect, the invention relates to a coaxial needle assembly for the placement of a cannula within a tissue prior to a biopsy procedure.

2. Description of the Related Art

A biopsy is a well-known medical procedure that involves taking a sample of tissue from a person and examining it for diagnostic purposes. The biopsy is often done when an abnormality, such as a lesion, is found in a tissue mass, using an imaging system, such as mammography or ultrasonography, or other methods of detection. While biopsies can be used for many different purposes, examining a sample of tissue from an abnormal site is one way to accurately diagnose whether the site is cancerous. In the case of suspected cancer, particularly cancer of the breast, early detection and diagnosis is critical to the success of the patient's treatment and recovery.

One biopsy technique frequently performed is a core biopsy, which uses a biopsy device in which a tissue specimen is captured in a coring cannula that is advanced into the tissue mass to the site of the abnormality. Some biopsy devices use a notched biopsy stylet that is inserted into a lesion, such that tissue prolapses into the notch on the biopsy stylet, with the coring cannula then advancing over the notch to cut a tissue sample. Other devices use just a coring cannula, which requires moving the end of the coring cannula to effect severing of the tissue sample from the surrounding tissue mass. Another device advances a spoon into the tissue mass, which is then followed by a coring cannula having a cutting finger, which is rotated to sever the tissue sample. Such a device can be found in commonly assigned U.S. Patent Application Publication No. 2006/0030785, entitled "Core Biopsy Device", which is incorporated herein by reference in its entirety. The biopsy cannula and stylet, if used, with the tissue sample, is then removed from the tissue, and the tissue sample is examined.

It is often necessary to take multiple tissue samples from the lesion and/or the surrounding area. To avoid having to puncture the skin for every tissue sample, a coaxial needle assembly is placed in the tissue prior to use of the biopsy device to act as a guide for the biopsy device. A coaxial needle assembly commonly includes a needle cannula defining a lumen in which a stylet is received to close off the open distal end of the needle cannula during insertion to prevent unwanted coring of the tissue. After insertion, the stylet is removed and the biopsy cannula and stylet/spoon of the biopsy device are inserted through the needle cannula and into the lesion to take a tissue sample. The biopsy device is then removed from the tissue, and the needle cannula can be manipulated to a new location within the tissue mass so that upon reinsertion of the biopsy device, a tissue sample can be taken from a different area of or surrounding the lesion.

The coaxial needle assembly is commonly placed using an imaging device. The placement normally locates the tip of the needle cannula at the desired location relative to the lesion. The biopsy device and needle cannula can be configured such that the biopsy device is aligned relative to the needle cannula to insure that upon actuation of the biopsy device, the biopsy specimen will be taken at a known distance from the tip of the needle cannula. A common way of accomplishing the alignment is to insert the biopsy device into the needle cannula until the biopsy device aligns with a reference point on the needle cannula. This can be done by aligning marks on the biopsy device and needle cannula or by inserting the biopsy device until it abuts the needle cannula. In most cases, the tip of the biopsy device's cannula/stylet is aligned with the tip of the needle cannula when the biopsy device and needle cannula are aligned. The reference points are external of the tissue mass, whereas the tips of the biopsy device and needle cannula are internal of the tissue mass, which provides the user with an externally visual method of aligning the internal tips, which are not visible other than using an imagining device.

The position of the needle cannula determines what tissue will be sampled by the biopsy device, since the biopsy cannula will protrude from the end of the needle cannula to take a tissue sample. Therefore, for current systems the alignment is dependent on the length of the needle cannula being the same as or a fixed length relative to the biopsy cannula prior to taking a tissue sample.

The current alignment approach is not compatible with biopsy devices having adjustable length biopsy specimens, especially those that increase the relative length of the cannula or stylet to adjust the length of the specimen. If the length of the biopsy device's cannula or stylet is extended/retracted relative to the supporting body to effect the specimen length adjustment and the abutment of the supporting body with the needle cannula is used for alignment, the biopsy device's cannula or stylet will be over/under inserted relative to the cannula needle. As such, it becomes necessary to account for the difference in lengths between the biopsy cannula and stylet and the needle cannula, which has a fixed length. This is difficult, since the user cannot view the position of the cannulas within the body and must rely upon external cues to verify that the biopsy cannula is correctly positioned within the needle cannula.

Another issue is that manufacturers of biopsy devices and coaxial needle assemblies often have unique ways of measuring the length of their respective cannulas. It is therefore difficult to use one manufacturer's biopsy device with another manufacturer's coaxial needle assembly.

SUMMARY OF THE INVENTION

In accordance with one aspect of the invention, a coaxial needle assembly for use with a biopsy device comprises a cannula defining a lumen and having a proximal end and a distal end, a stylet removably received within the lumen and having a proximal end and a distal end, and a throw calibrator adjustably carried by the cannula and having a biopsy device insertion stop, wherein the throw calibrator may be used to adjust the position of the insertion stop relative to the cannula to calibrate the coaxial needle assembly with the throw distance of the biopsy device.

In accordance with another aspect of the invention, a biopsy device system for the percutaneous removal of a specimen from an area of interest within a tissue mass is disclosed. The biopsy device system comprises a variable throw biopsy device having a needle assembly with an adjustable throw distance, a guide cannula defining a lumen and having a proximal end and a distal end, and a throw calibrator adjustably carried by the guide cannula and having a biopsy device insertion stop, wherein the throw calibrator may be used to adjust the position of the insertion stop relative to the guide cannula to calibrate the guide cannula with the throw distance of the biopsy device.

BRIEF DESCRIPTION OF THE DRAWINGS

In the drawings:

FIGS. 6A-6B are cross-sectional views through the coaxial needle assembly from FIG. 1, illustrating the movement of the throw calibrator along the cannula assembly.

FIG. 7D is a cross-sectional view of a biopsy device inserted into the coaxial needle assembly.

FIGS. 9A-9B are cross-sectional views through the biopsy device system from FIG. 8, with the coaxial needle assembly received on the biopsy device to calibrate the coaxial needle assembly with the throw distance of the biopsy device.

DESCRIPTION OF THE PREFERRED EMBODIMENT

Figure 1:
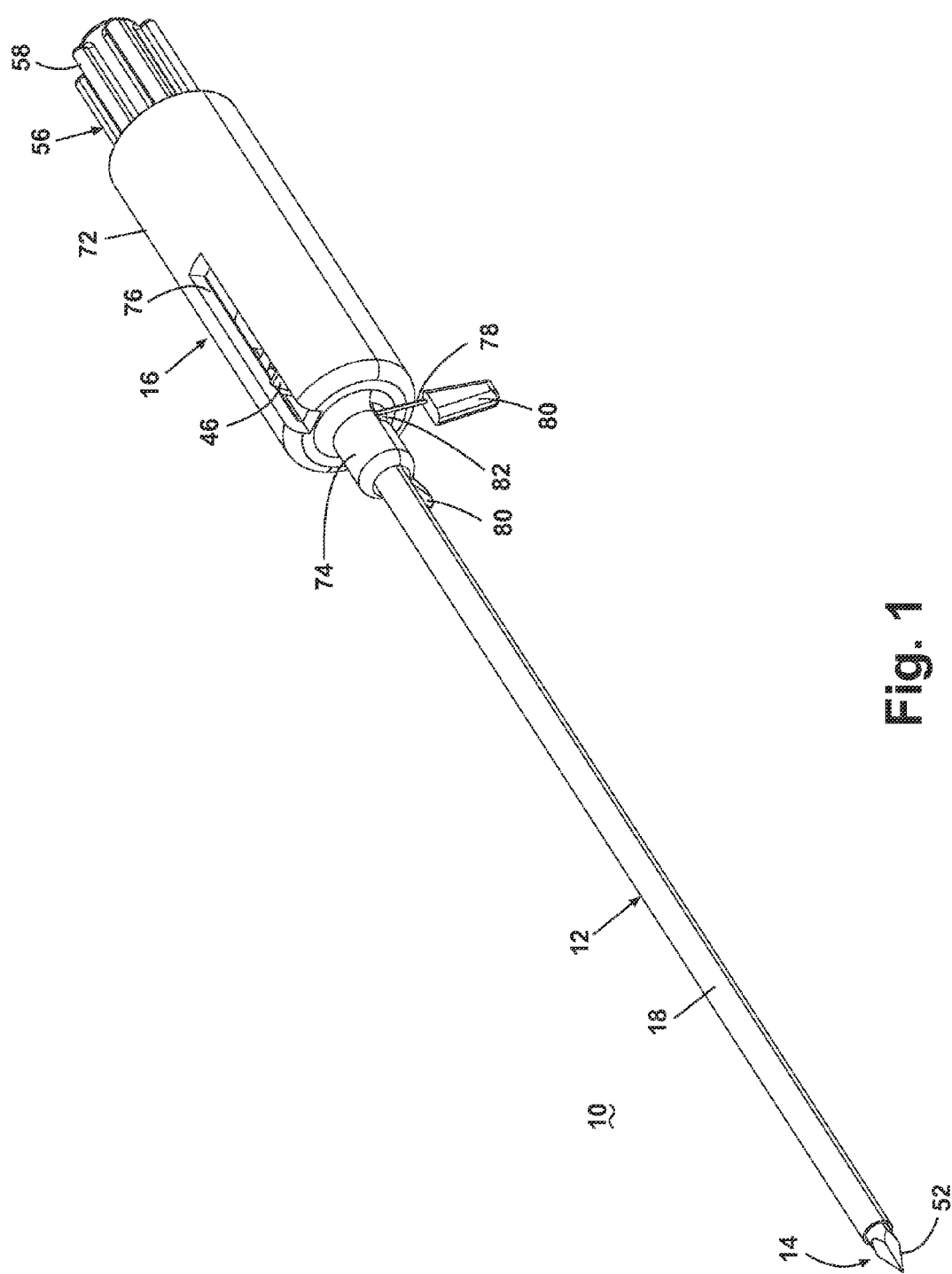
FIG. 1 is a perspective view of a coaxial needle assembly comprising a cannula assembly, a stylet assembly, and a throw calibrator according to a first embodiment of the invention.
Figure 2:
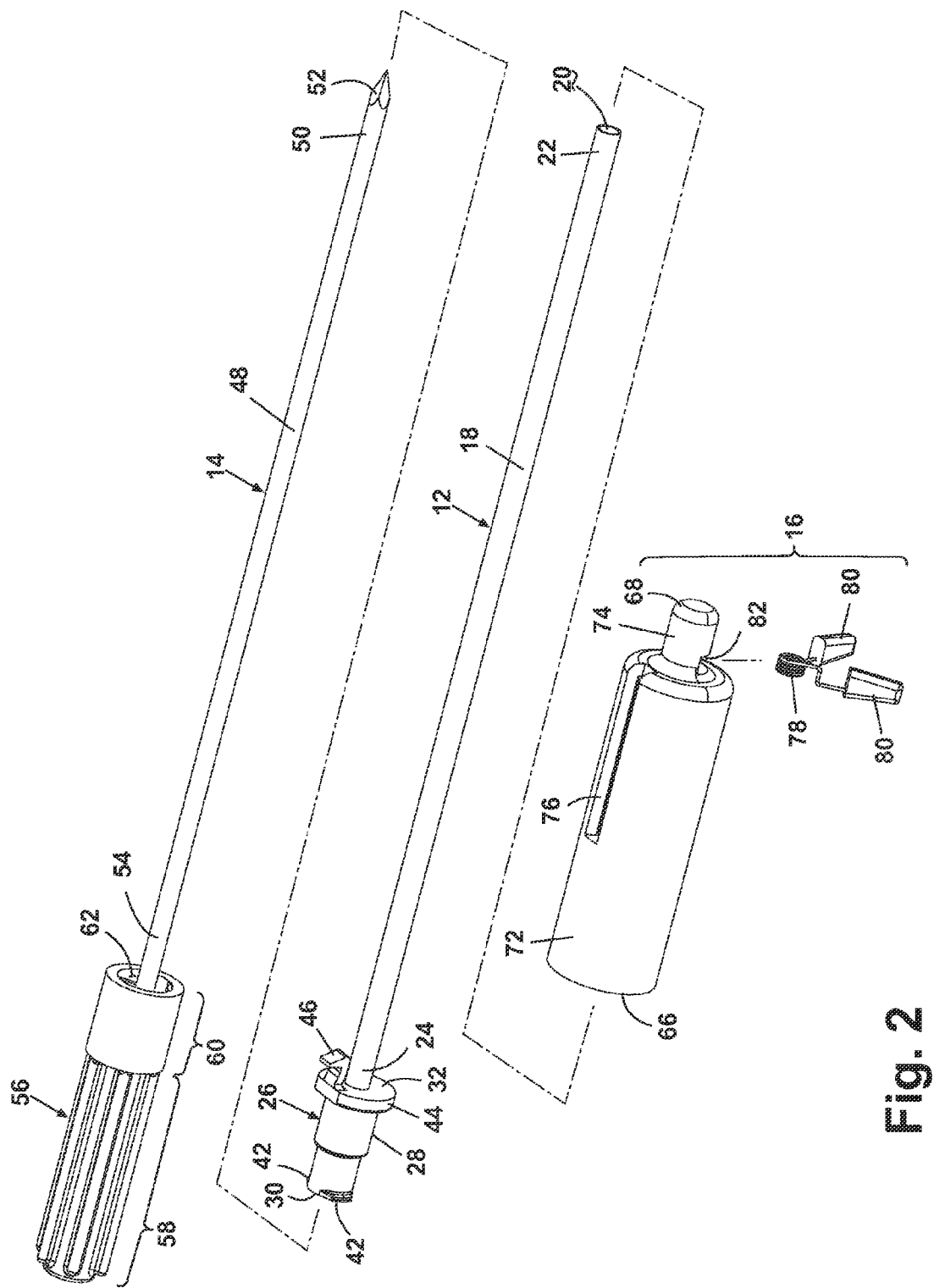
FIG. 2 is an exploded view of the coaxial needle assembly from FIG. 1.

Referring to FIGS. 1-2, a coaxial needle assembly 10 according to a first embodiment of the invention is illustrated, and comprises a cannula assembly 12, a stylet assembly 14, and an adjustable body comprising a throw calibrator 16 that is used to calibrate the coaxial needle assembly 10 with the throw of a biopsy device. The stylet assembly 14 is selectively coaxially received by the cannula assembly 12, which is in turn selectively coaxially received by the throw calibrator 16. As used herein with respect to the coaxial needle assembly 10, the terms "distal" and "forward" refer to or in a direction toward that end of the coaxial needle assembly 10 that is directed toward a lesion and away from a user. "Proximal" or "rearward" thus refers to or in a direction toward that end of the coaxial needle assembly 10 that is directed away from the lesion and toward the user. It is also understood that some of the drawings are not to scale, in order to clearly illustrate the various features of the invention.

Figure 3:
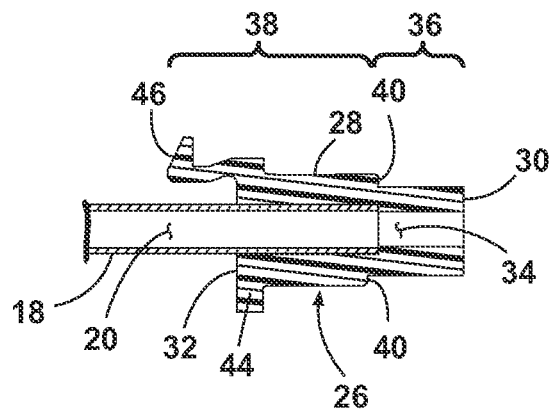
FIG. 3 is a close-up cross-sectional view of the cannula assembly from FIG. 1.

Referring to FIGS. 1-3, the cannula assembly 12 comprises a guide cannula 18 defining a lumen 20 and having an open distal end 22 and an open proximal end 24. A cannula hub 26 is attached to the outer surface of the guide cannula 18 near the open proximal end 24. The cannula hub 26 comprises a cylindrical body 28 having a rearward end wall 30 and a forward end wall 32, and a hollow interior 34 extending though the cylindrical body 28 to accommodate the guide cannula 18 and the stylet assembly 14.

The cylindrical body 28 includes a proximal section 36 joined to a distal section 38 that is of slightly greater diameter than the proximal section 36 to form a stylet hub engaging surface 40 that faces rearwardly. A pair of opposing rearward end flanges 42 extend partially around the periphery of the proximal section 36, adjacent the rearward end wall 30, and a forward end flange 44 extends around the periphery of the distal section 38, adjacent the forward end wall 44. A flexible detent 46 is formed on the forward end flange 44 and projects distally of the forward end wall 32.

Figure 4:
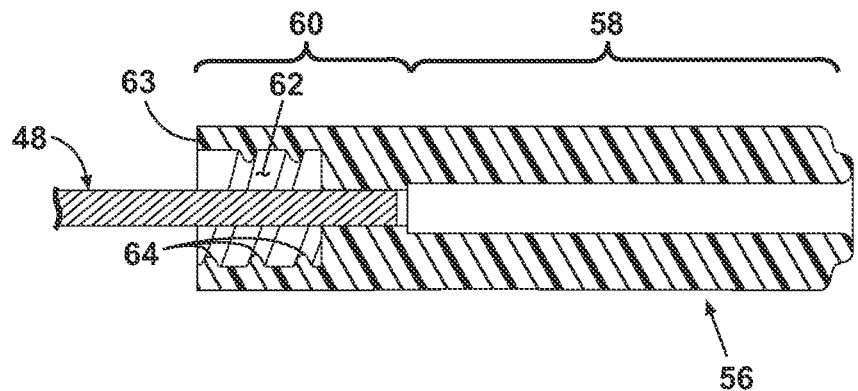
FIG. 4 is a close-up cross-sectional view of the stylet assembly from FIG. 1.

Referring to FIGS. 1-2 and 4, the stylet assembly 14 comprises a needle or stylet 48 having a distal end 50 defining an insertion tip 52 and a proximal end 54. A stylet hub 56 is attached to the stylet 48 near the proximal end 54 and can be releasably coupled with the cannula hub 26. The stylet hub 56 comprises a proximal handle section 58, which a user can grip to manipulate the stylet assembly 14, joined with a distal receiving section 60 having a hollow interior 62 which receives the proximal section 36 of the cannula hub 36 and a forward end wall 63. The hollow interior 62 comprises screw threads 64 that are engaged by the rearward end flange 42 by rotating the proximal section 36 within the hollow interior 62 to releasably fasten the stylet assembly 14 to the cannula assembly 12.

Figure 5:
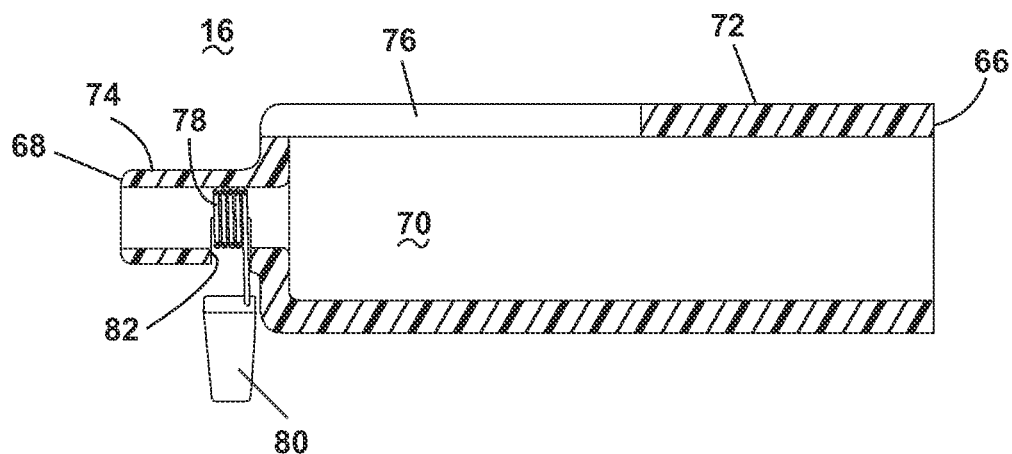
FIG. 5 is a close-up cross-sectional view of the throw calibrator from FIG. 1.

Referring to FIGS. 1-2 and 5, the throw calibrator 16 comprises generally cylindrical body that encircles the guide cannula 18 and can slidably move relative to the guide cannula 18. The throw calibrator can comprise an insertion stop 66 for arresting the insertion of a biopsy device needle assembly into a tissue mass. By adjusting the position of the insertion stop 66 relative to the cannula assembly 12 (in this case by axially moving the throw calibrator 16), the coaxial needle assembly 10 can be calibrated with the throw of a biopsy device.

As illustrated herein, the throw calibrator 16 comprises a proximal or rearward end wall 66 that acts as the insertion stop 66, a distal or forward end wall 68, and a hollow interior 70 extending though the throw calibrator 16 to accommodate the cannula assembly 12 and the stylet assembly 14. The throw calibrator 16 includes a proximal cylindrical section 72 joined to a distal nose section 74 that has a smaller diameter than the cylindrical section 72. An elongated slot 76 is formed on the cylindrical section 72 and slidingly receives the detent 46 on the cannula assembly 12 to prevent the cannula assembly 12 from rotating with respect to the throw calibrator 16 and to guide the longitudinal movement of the cannula assembly 12 relative to the throw calibrator 16. The length of the elongated slot 76 further determines the range of movement of the throw calibrator 16 relative to the cannula assembly 12. The length of the elongated slot 76 can selected such that the range of movement of the throw calibrator 16 corresponds to the range of possible throw distances of a biopsy device.

The hollow interior 70 of the throw calibrator 16 receives a releasable lock that fixes the position of the throw calibrator 16 in relation to the cannula assembly 12, and, as illustrated herein, includes a torsion spring 78 having spring arms 80 that protrude through an opening 82 formed in the nose section 74. When assembled, the guide cannula 18 is slidably received through the torsion spring 78 to releasably fix the position of the throw calibrator 16 along the guide cannula 18. Squeezing the spring arms 80 releases the torsion spring 78 relative to the guide cannula 18, permitting the throw calibrator 16 to be slid along the guide cannula 18 until the spring arms 80 are released.

Referring to FIGS. 6A-6B, the coaxial needle assembly 10 can be calibrated with the throw distance of a biopsy device by moving the throw calibrator 16 relative to the cannula assembly 12. This adjusts the effective length of the guide cannula 18, which is the distance between the open distal end 22 and the insertion stop 66 of the throw calibrator 16. This also adjusts the distance the stylet 48 protrudes with respect to the throw calibrator 16, since the insertion of the stylet 48 within the guide cannula 18 is limited by the abutment of the forward end wall 63 against the stylet hub engaging surface 40. The effective length of the guide cannula 18 is adjusted by pressing the spring arms 80 toward each other to expand the torsion spring 78 and loosen its grip on the guide cannula 18, allowing the throw calibrator 16 to be translated along the cannula assembly 12. The range of movement of the throw calibrator 16 relative to the cannula assembly 12 is limited by the length of the slot 76 in which the detent 46 moves. As shown in FIG. 6A, the guide cannula 18 is at a minimum effective length in the position where the detent 46 abuts the forward portion of the slot 76. As shown in FIG. 6B, the guide cannula 18 is at a maximum effective length in the position where the detent 46 abuts the rearward portion of the slot 76. It is understood that the effective length of the guide cannula 18 is infinitely adjustable between the positions illustrated in FIGS. 6A-6B because the position of the throw calibrator 16 is infinitely adjustable. It is also understood that the cannula assembly 12 and stylet assembly 14 can be moved as a unit, while keeping the throw calibrator 16 relatively still. The throw calibrator 16, or another portion of the coaxial needle assembly 10, can further be provided with indicia (not shown), such as distance markings or a digital display, for enabling the length of coaxial needle assembly 10 to be adjusted a predetermined distance.

Figure 8:
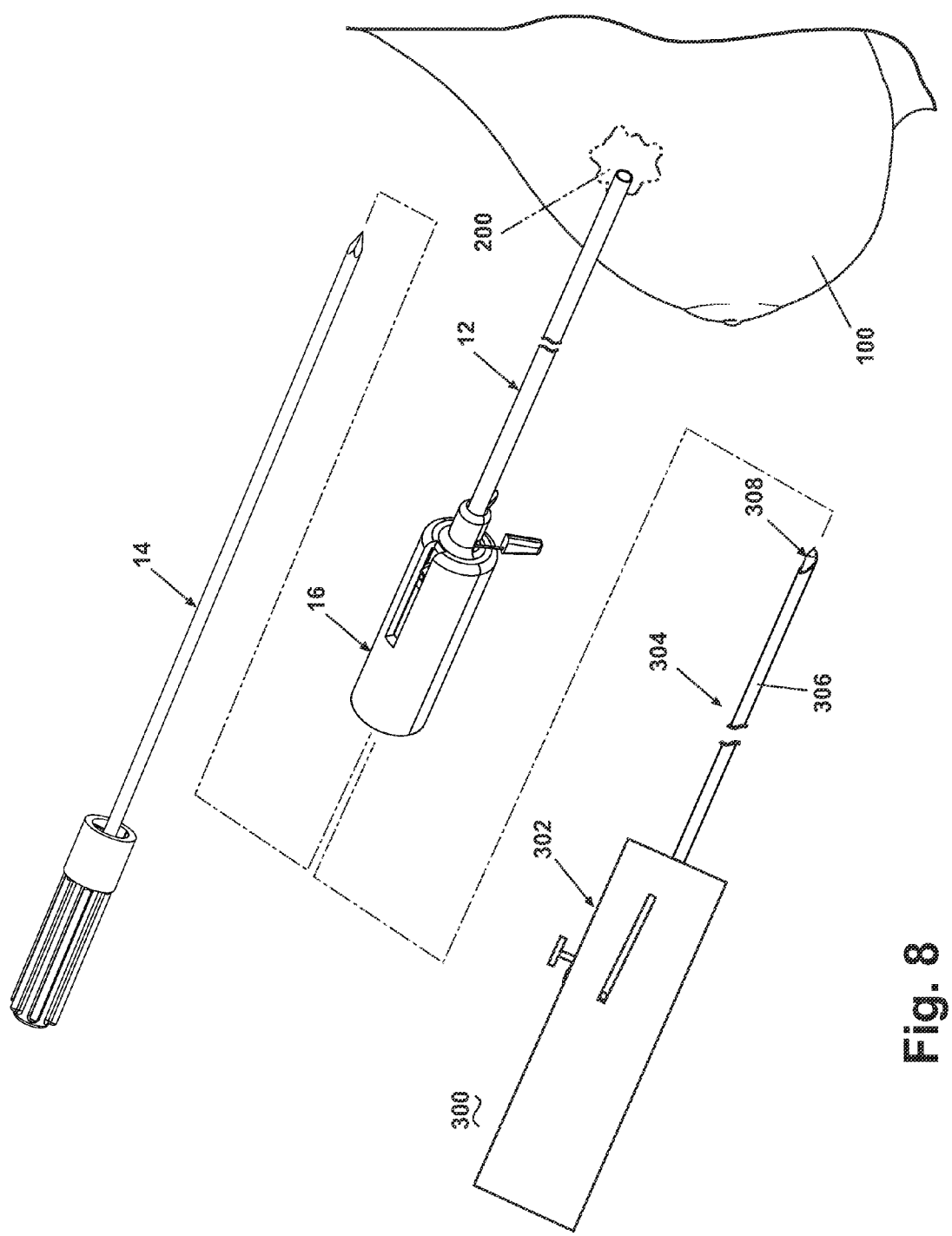
FIG. 8 is a perspective view of a biopsy device system comprising the coaxial needle assembly from FIG. 1 inserted to the lesion and a biopsy device comprising a biopsy needle assembly for obtaining a biopsy sample from the lesion by inserting the needle assembly through the cannula assembly.

FIG. 8 illustrates one example of a biopsy device system for the percutaneous removal of a specimen from an area of interest within a tissue mass 100, in which the coaxial needle assembly 10 is used in conjunction with a biopsy device 300. An exemplary biopsy device 300 comprises a actuator assembly 302 structurally and operably connected to a biopsy needle assembly 304 which is used to penetrate the tissue mass 100 to obtain a biopsy sample from an area of interest comprising a lesion 200. The biopsy needle assembly 304 includes a biopsy cannula 306 and a biopsy stylet 308 which is received by the biopsy cannula 306 in coaxially telescoping relationship. The biopsy needle assembly 304 has a throw distance, which is the distance the biopsy stylet 306 travels relative to the biopsy cannula 306 when fired, and which determines the size or length of the specimen obtained.

The biopsy device 300 can comprise a variable throw biopsy device having an adjustable throw distance to permit the user to select the size or length of the specimen obtained. As illustrated herein, the biopsy device 300 comprises an adjustable biopsy stylet 308 and a biopsy cannula 306 with a fixed extension distance. Since the length of the tissue sample is set by the distance from the tip of the stylet 308 to the tip of the cannula 306 when the stylet 308 has been fired, this distance can be adjusted by extending or retracting the stylet 308. Thus, adjusting the throw of the biopsy device 300 also adjusts the size or length of the specimen obtained. Since the guide cannula 18 is adjustable in effective length, it can advantageously accommodate for the adjusted length of the biopsy stylet 308. In use, the throw distance of the biopsy stylet 308 is set first, and then the coaxial needle assembly 10 is calibrated with the set length of the biopsy stylet 308.

Referring to FIGS. 9A-9B, one expeditious way of calibrating the coaxial needle assembly 10 is to insert the assembled cannula assembly 12 and throw calibrator 16, without the stylet assembly 14, over the biopsy needle assembly 304 until the actuator assembly 302 abuts the insertion stop 66, as shown in FIG. 9A. The throw calibrator 16 is then adjusted along the cannula assembly 12 until the distal tip of the biopsy needle assembly 304 and the open distal end 22 of the guide cannula 18 are in a suitable predetermined relationship for insertion into the tissue mass, as shown in FIG. 9B. One suitable predetermined relationship is one in which the distal tip of the biopsy stylet 308 being flush with the open distal end 22 of the guide cannula 18, which makes the effective length of the cannula assembly 12 equal to the length of the biopsy stylet 308. Another suitable predetermined relationship is one in which the distal tip of the biopsy cannula 306 being flush with the open distal end 22 of the guide cannula 18, which makes the effective length of the cannula assembly 12 equal to the length of the biopsy cannula 306. Both relationships guarantee that the tissue at the end of the guide cannula 18 will be sampled. Another suitable predetermined relationship is one in which the distal tip of the biopsy needle assembly 304 closes the open distal end 22 of the guide cannula 18, which insures that tissue will not prolapse into the guide cannula 18. The coaxial needle assembly 10 is then removed from the biopsy device 200 and the stylet assembly 14 is reassembled to the coaxial needle assembly 10, readying it for insertion in the tissue mass 100.

Another way of calibrating the coaxial needle assembly 10 is to simply determine the throw distance of the biopsy device 300 and set the effective length in accordance with the throw distance using indicia provided on the guide cannula. This is especially effective if the indicia directly correlate with the possible throw distances on the biopsy device 300.

Figure 7A:
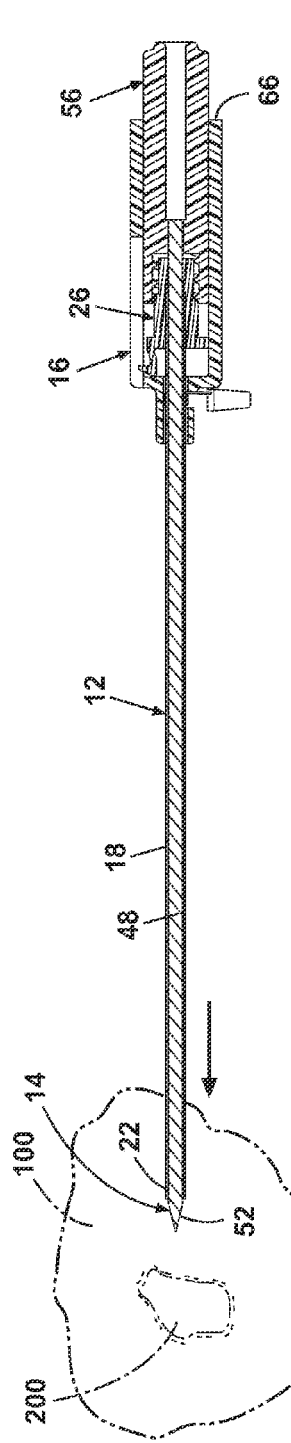
FIG. 7A is a cross-sectional view of the coaxial needle assembly inserted into a tissue mass having a lesion.
Figure 7B:
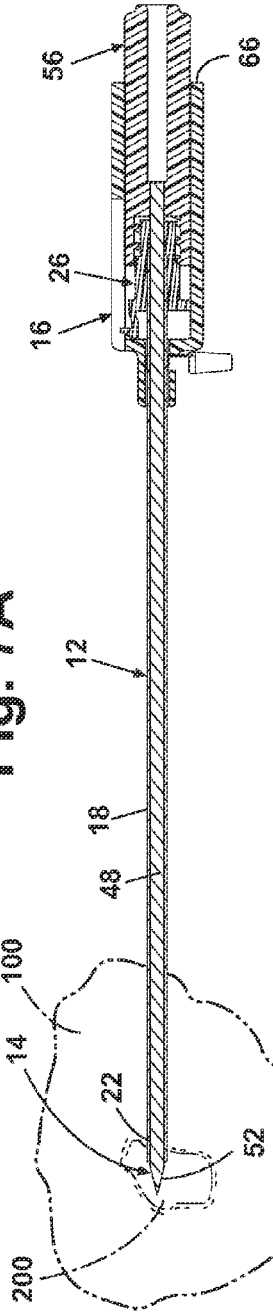
FIG. 7B is a cross-sectional view of the coaxial needle assembly inserted into the lesion in the tissue mass.
Figure 7C:
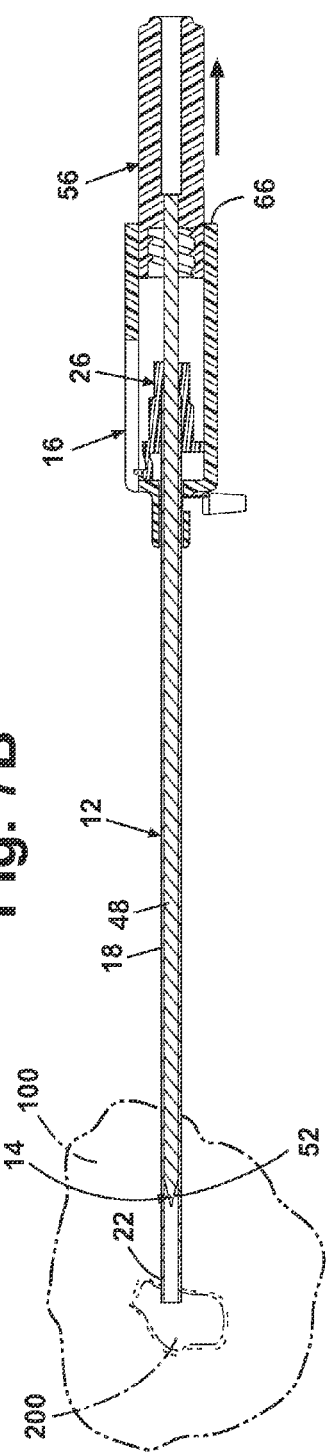
FIG. 7C is a cross-sectional view of the stylet assembly of the coaxial needle assembly withdrawn from the tissue mass, leaving the cannula assembly and throw calibrator in place.

Referring to FIGS. 7A-7C, the coaxial needle assembly 10 is illustrated within a tissue mass 100 having a lesion 200 to show the various steps in the process of placing the coaxial needle assembly 10 at the lesion 200 prior to using a biopsy device to obtain a tissue sample from the lesion 200. Prior to insertion, the coaxial needle assembly 10 is calibrated with the throw distance of the biopsy device as discussed above by moving the throw calibrator 16 along the guide cannula 18 to set the effective length of the guide cannula 18. As shown in FIG. 7A, the coaxial needle assembly 10 is inserted into the tissue mass 100 with the stylet assembly 14 coaxially received by and coupled to the cannula assembly 12, such that the stylet 48 is received within the lumen 20 and protrudes slightly from the open distal end 22 of the guide cannula 18, with the insertion tip 52 leading the coaxial needle assembly 10 through the tissue mass 100.

As shown in FIG. 7B, the coaxial needle assembly 10 is positioned so that the insertion tip 52 is at or near the lesion 200. Preferably, the coaxial needle assembly 10 is positioned by using an imaging system. The coaxial needle assembly 10 can be designed for enhanced visibility using common imaging systems, such as CAT scan, ultrasonography and mammography. For example, a portion of the coaxial needle assembly 10 can be enhanced for ultrasound detection by forming an echogenicity enhancement on either the guide cannula 18 or the stylet 48. Once such enhancement is disclosed in U.S. Pat. No. 5,820,554 to Davis et al., incorporated herein by reference in its entirety.

As shown in FIG. 7C, once the coaxial needle assembly 10 is positioned, the stylet assembly 14 is unlocked from the cannula assembly 12 and withdrawn from the tissue mass 100, thereby removing the stylet assembly 14 from rest of the coaxial needle assembly 10. The stylet assembly 14 is unlocked by rotating the stylet hub 56 relative to the cannula assembly 12 to unscrew the rearward end flanges 42 from the screw threads 64.

Referring to FIG. 7D, after placement of the coaxial needle assembly 10 at the lesion 200 and withdrawal of the stylet assembly 14, as illustrated in FIGS. 7A-7C, the biopsy needle assembly 304 is inserted through the lumen 20 of the guide cannula 18 until it meets the insertion stop 66. Since the effective length of the guide cannula 18 has been calibrated with the throw distance of the biopsy device 300, the biopsy needle assembly 304 and the guide cannula 18 are in a suitable predetermined relationship; in this case, the tip of the biopsy stylet 308 will protrude slightly from the open distal end 22 of the guide cannula 18 into the lesion 200. This is extremely beneficial to the technician taking the biopsy specimen as one cannot see the location of the tip of the biopsy device 300 as it is in the tissue mass, but still knows that the physical relationship between the cannula guide 18 and biopsy device 300 will result in the biopsy device 300 being properly located. This will negate the need for the technician to re-image the location of the biopsy device 300 after insertion. It will also simplify the taking of multiple specimens, which requires the withdrawal and reinsertion of the biopsy device 300.

Figure 10:
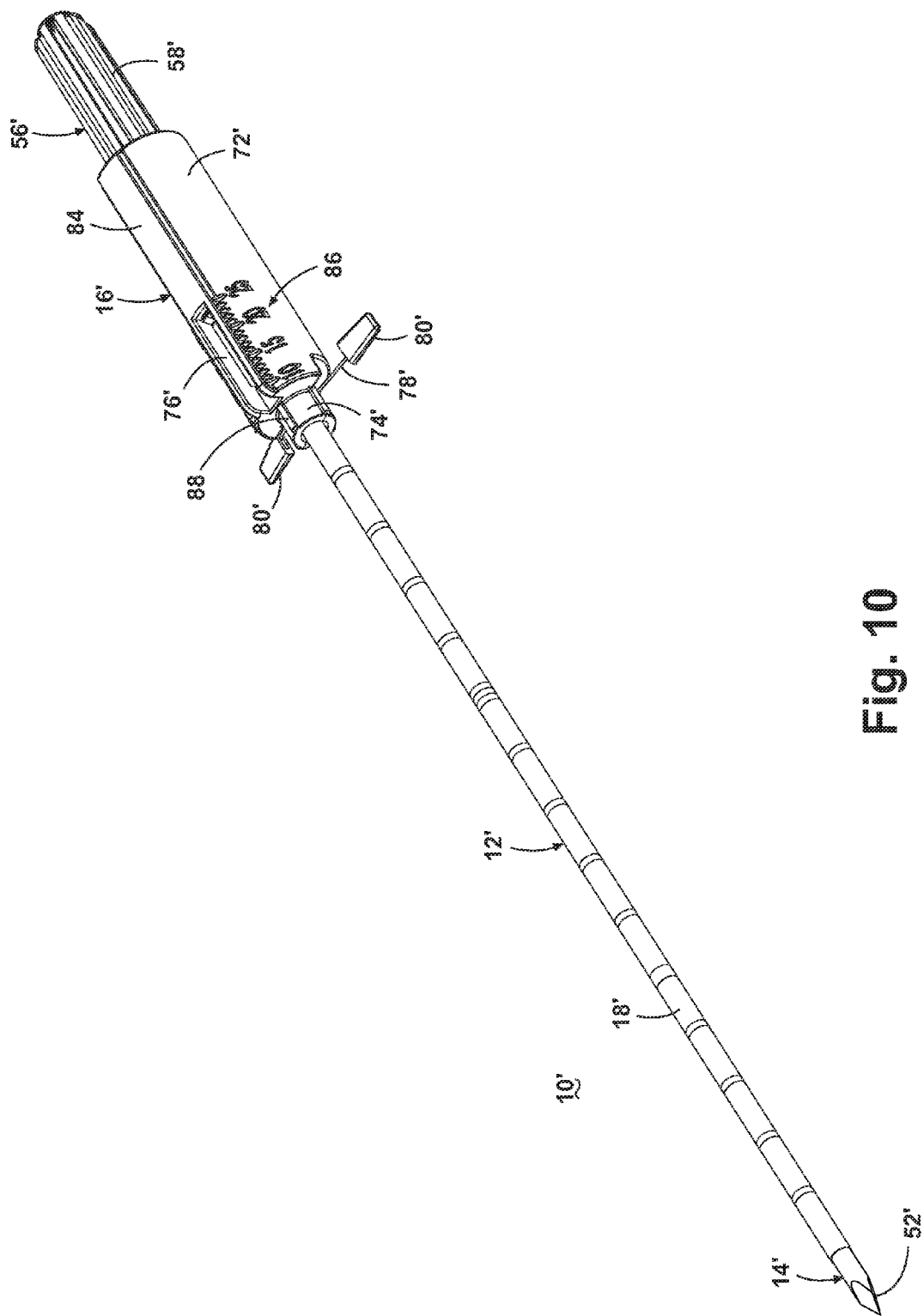
FIG. 10 is a perspective view of a coaxial needle assembly comprising a cannula assembly, a stylet assembly, and a throw calibrator according to a second embodiment of the invention.
Figure 11:
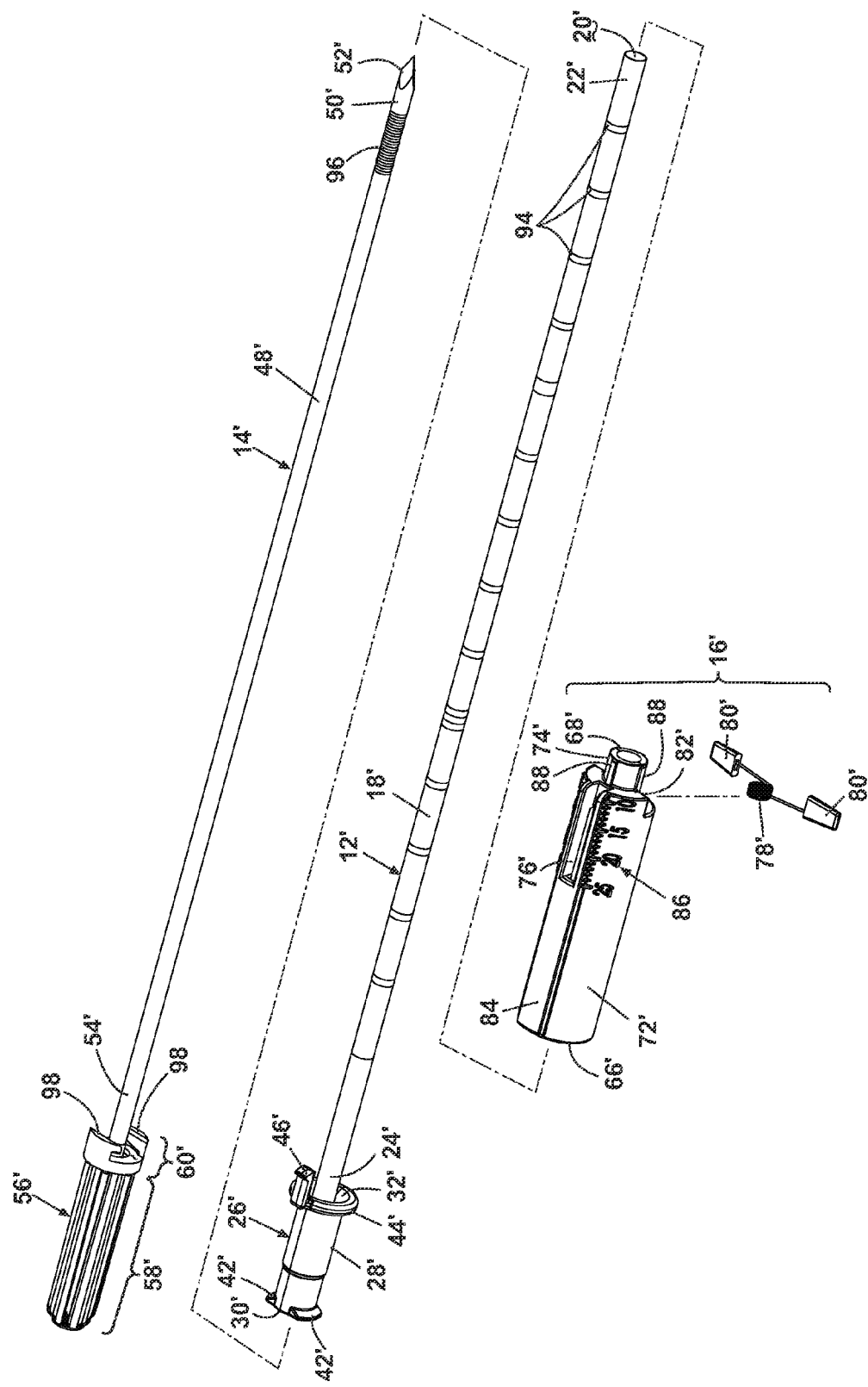
FIG. 11 is an exploded view of the coaxial needle assembly from FIG. 9.

Referring to FIGS. 10-11, a coaxial needle assembly 10' according to a second embodiment of the invention is illustrated, with like elements being identified by like numerals bearing a prime (') symbol. The structure and the method of using the second embodiment is substantially similar to the structure of method of using the first embodiment, so the discussion of the second embodiment will be limited to the differences between the two embodiments. Whereas the throw calibrator 16 shown in FIGS. 1-2 had a generally uniformly cylindrical proximal section 72, the throw calibrator 16' has a protruded area 84 on the proximal section 72', which allows for easier removal of the cannula assembly 14' from the throw calibrator 16'. The elongated slot 76' is formed on the protruded area 84. Additionally, indicia comprising a set of distance markings 86 is provided on the proximal section 72' adjacent the elongated slot 76'. The distance markings 86 enable the effective length of guide cannula 18' to be adjusted a predetermined amount, with or without the guide cannula 18' being inserted over a needle assembly of a biopsy device. The distance markings 86 can directly or indirectly correspond to the throw of a biopsy device, such that the distance markings 86 can be used to calibrate the coaxial needle assembly 10 with the throw distance of a biopsy device.

Figure 12:
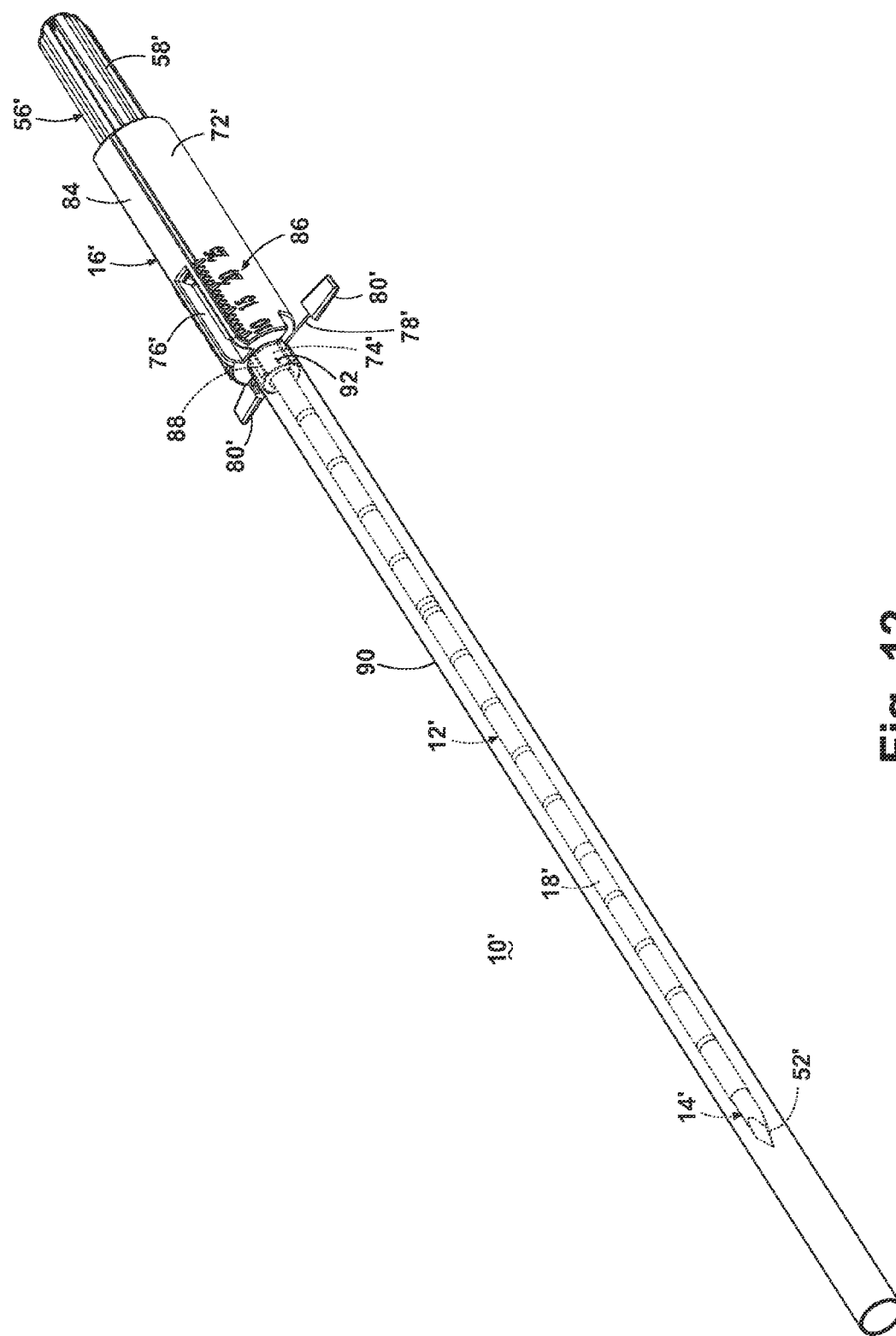
FIG. 12 is a perspective view of the coaxial needle assembly from FIG. 9 with a distal tip protector disposed on the throw calibrator.

The throw calibrator 16' further comprises at least one rib 88 formed on the nose section 74 for frictionally engaging a tip protector 90, shown in FIG. 12 which is a sleeve-like device commonly used to cover a needle assembly when not in use, and can be temporarily press fit over the nose section 74. When the tip protector 90 is received on the nose section 74, the spaces between adjacent ribs 88 form passageways 92 through which a sterilization fluid, such as ethylene oxide (EtO) gas, can flow between the coaxial needle assembly 10' and the tip protector 90.

The guide cannula 18 and the stylet 48 are provided with at least one marker for enhanced visibility using common imaging systems. As illustrated herein, the guide cannula 18 comprises multiple spaced markers on its exterior that are spaced at regular intervals, such as every 1 cm, and the stylet 48 comprises a marking 96 near or at its distal end 50', which can comprise an echogenicity enhancement as disclosed in the Davis patent.

Figure 13A:
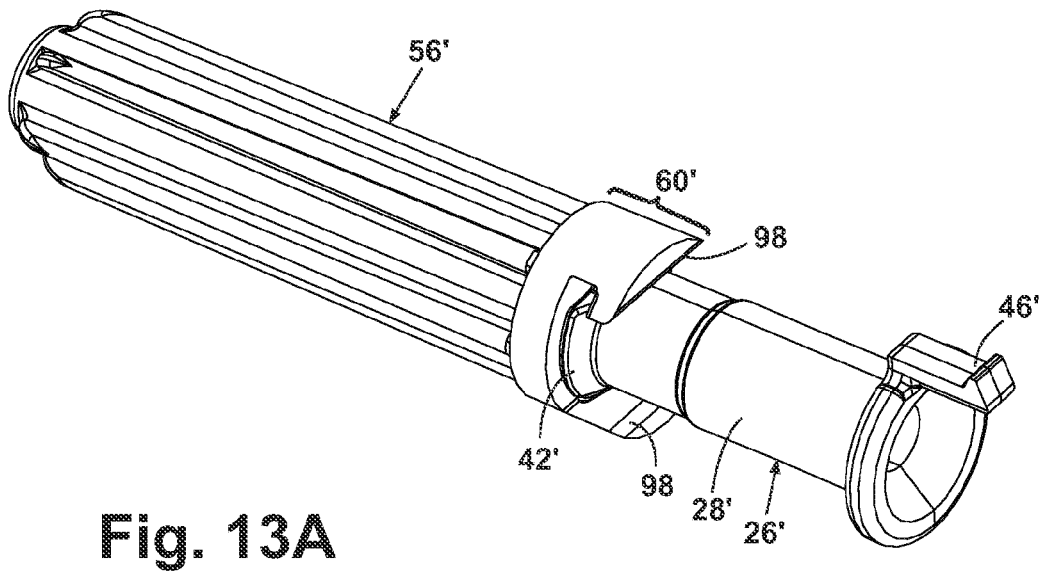
FIG. 13A is a close-up perspective view of a luer lock coupling for the cannula assembly and stylet assembly in an uncoupled or unlocked position.
Figure 13B:
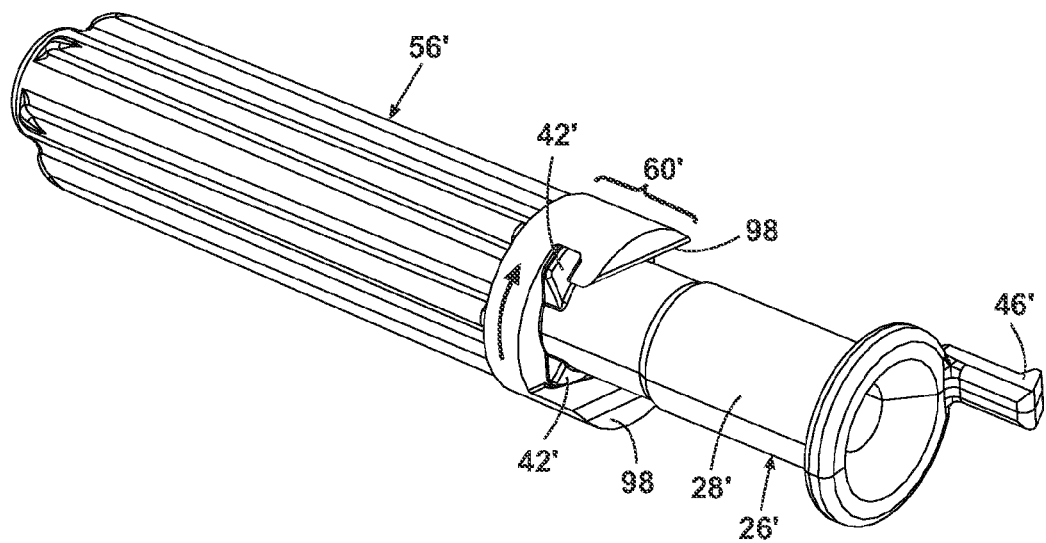
FIG. 13B is a close-up perspective view of the luer lock coupling in a coupled or locked position.

Referring to FIGS. 13A-13B, the stylet hub 56' is coupled with the cannula hub 26' by a luer lock coupling, which provides a fluid-tight coupling between the hub 26', 56' and allows the user to optionally inject fluid through the coaxial needle assembly 10'. The distal receiving section 60' of the stylet hub 56' comprises two opposed arms 98 which engage the flanges 42' on the cannula hub 26' to releasably fasten the stylet assembly 14' to the cannula assembly 12'. The stylet assembly 14' is coupled or locked to the cannula assembly 12' by rotating the stylet hub 26' relative to the cannula hub 56' until the arms 98 engage the flanges 42', as shown in FIG. 13B.

Figure 14:
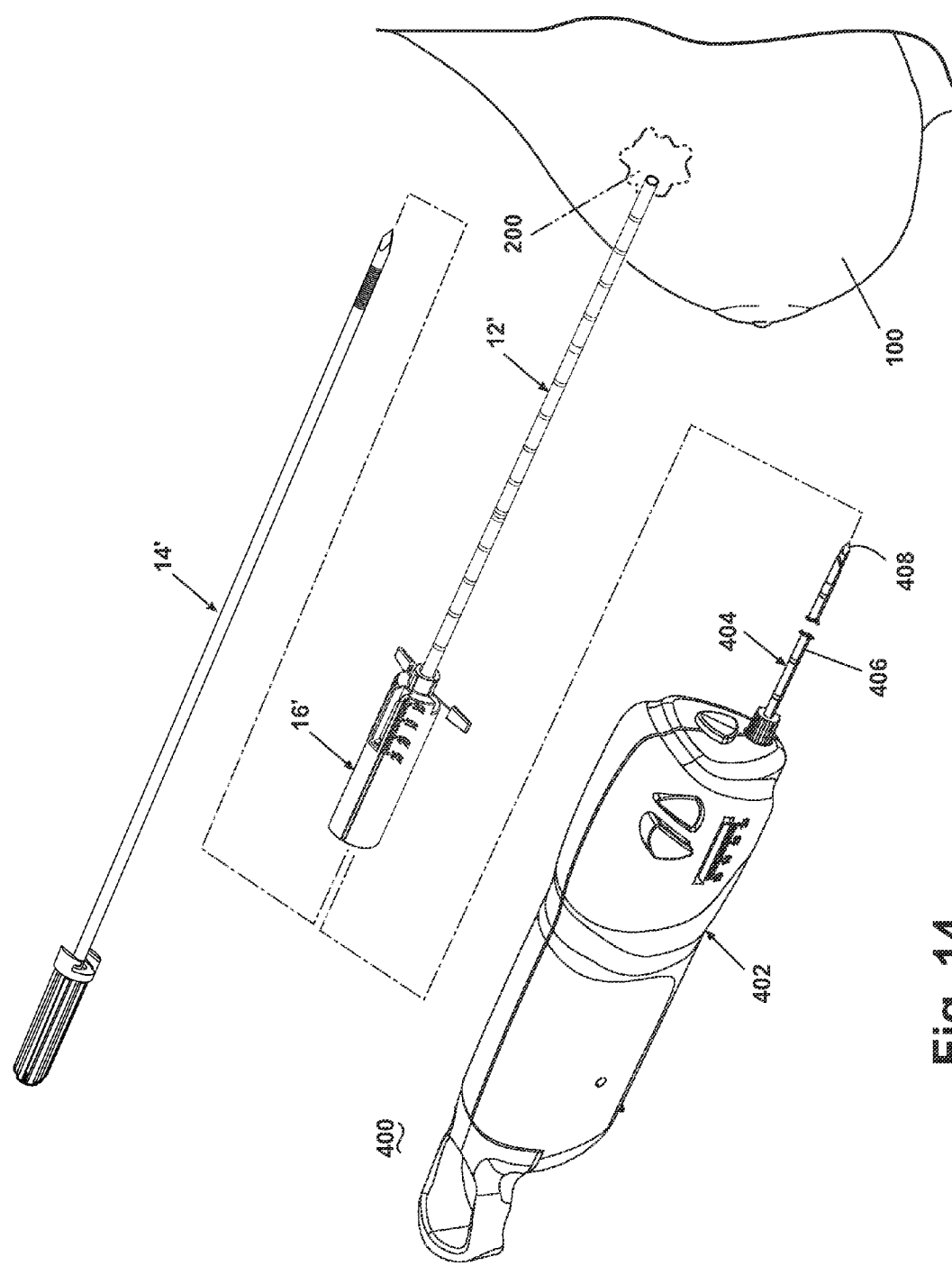
FIG. 14 is a perspective view of a biopsy device system comprising the coaxial needle assembly from FIG. 10 inserted to the lesion and a biopsy device comprising a biopsy needle assembly for obtaining a biopsy sample from the lesion by inserting the needle assembly through the cannula assembly.

FIG. 14 illustrates one example of a biopsy device system for the percutaneous removal of a specimen from an area of interest within a tissue mass 100, in which the coaxial needle assembly 10' is used in conjunction with a variable throw biopsy device 400. The exemplary variable throw biopsy device 400 comprises a actuator assembly 402 structurally and operably connected to a biopsy needle assembly 404 which is used to penetrate the tissue mass 100 to obtain a biopsy sample from an area of interest comprising a lesion 200. The biopsy needle assembly 404 includes a biopsy cannula 406 and a biopsy stylet 408 which is received by the biopsy cannula 406 in coaxially telescoping relationship. The biopsy needle assembly 404 has an adjustable throw distance, which is the distance the biopsy stylet 406 travels relative to the biopsy cannula 406, to permit the user to select the size or length of the specimen obtained. Examples of a suitable variable throw biopsy device are disclosed in U.S. Pat. No. 8,197,419, issued Jun. 12, 2012, and its priority document, U.S. Provisional Application No. 61/057,378, filed May 30, 2008, both of which are incorporated herein by reference in their entirety, in which the position of a throw stop (not shown) is adjusted to set the throw distance, i.e. the distance the biopsy stylet 406 can travel when fired. Another example of a suitable variable throw biopsy device is disclosed in U.S. patent application Ser. No. 10/908,427, filed May 11, 2005, now U.S. Pat. No. 8,088,081, issued Jan. 3, 2012, which is incorporated herein in its entirety.

It is understood that the coaxial needle assembly 10, 10' of the invention could be used with a biopsy device having a coring cannula and a non-notched stylet. In such a variation, the throw distance of the core biopsy device would be the distance the coring cannula travels past the stylet. The throw distance would be roughly equal to the distance the distal edge of the coring cannula projects past the distal tip of the stylet when fired.

The adjustable coaxial needle assembly 10 allows the user to adjust the location of the throw calibrator 16 along the cannula assembly 12 and maintain a predetermined correct relationship between the cannula and stylet distal ends 22, 50 that is suitable for insertion of the coaxial needle assembly 10 into a tissue mass. One example of a relationship suitable for insertion of the coaxial needle assembly 10 into a tissue mass is one in which the distal end 50 or insertion tip 52 of the stylet assembly 12 closes the open distal end 22 of the cannula assembly 12 to prevent tissue from entering the lumen 20. The ability to adjust the effective length of the cannula assembly and maintain a correct predetermined relationship between the stylet and cannula ends is desirable because the coaxial needle assembly 10 can accommodate the moving stylet of a variably throw biopsy device, insuring that a correct sample size is obtained. The coaxial needle assembly 10 can also be used with non-variable throw biopsy devices, and has the advantage of being usable with a variety of biopsy devices having different throw distances.

While the invention has been specifically described in connection with certain specific embodiments thereof, it is to be understood that this is by way of illustration and not of limitation, and the scope of the appended claims should be construed as broadly as the prior art will permit.

What is claimed is:

1. A coaxial needle assembly for use with a variable throw biopsy device having a needle assembly comprising a biopsy cannula and a biopsy stylet which is received by the biopsy cannula in coaxially telescoping relationship and a throw distance comprising the distance the biopsy stylet travel relative to the biopsy cannula when the biopsy device is fired, the coaxial needle assembly comprising:
    a cannula defining a lumen adapted to receive the needle assembly of the biopsy device and having a proximal end and a distal end;
    a stylet removably received within the lumen and having a proximal end and a distal end; and
    a throw calibrator adjustably carried by the cannula and having a proximal end and a distal end, the proximal end and defining a biopsy insertion stop adapted to arrest the insertion of the needle assembly into a tissue mass by abutting a portion of the biopsy device against the insertion stop;
    wherein the throw calibrator may be used to adjust the position of the insertion stop relative to the cannula to calibrate the coaxial needle assembly with the throw distance of the biopsy device.

2. The coaxial needle assembly according to claim 1 wherein the throw calibrator comprises an elongated slot and the cannula has a detent that is received in the slot to permit relative longitudinal movement between the throw calibrator and the cannula, whereby the length of the elongated slot determines the range of movement of the throw calibrator relative to the cannula.

3. The coaxial needle assembly according to claim 2 wherein the length of the elongated slot is selected such that the range of movement of the throw calibrator relative to the cannula corresponds to the range of possible throw distances of the biopsy device.

4. The coaxial needle assembly according to claim 1 wherein the throw calibrator further comprises a releasable lock to releasbly fix the position of the insertion stop along the cannula.

5. The coaxial needle assembly according to claim 4 wherein the releasable lock comprises a torsion spring carried by the throw calibrator and encircling the cannula.

6. The coaxial needle assembly according to claim 1 wherein the throw calibrator comprises a cylindrical body that encircles the cannula and slidably moves relative to the cannula, the cylindrical body comprising the proximal and distal ends of the throw calibrator.

7. The coaxial needle assembly according to claim 6 wherein the slidable adjustment of the cylindrical body adjusts the effective length between the proximal end defining the insertion stop and the distal end of the cannula.

8. The coaxial needle assembly according to claim 7 wherein the cylindrical body comprises indicia that correspond to the throw distance of the biopsy device such that the indicia can be used to calibrate the coaxial needle assembly with the throw distance of the biopsy device.

9. The coaxial needle assembly according to claim 1 wherein the cannula further comprises a cannula hub attached to the proximal end of the cannula and the stylet further comprises a stylet hub attached to the proximal end of the stylet and the stylet hub is releasably coupled with the cannula hub.

10. The coaxial needle assembly according to claim 9 wherein the stylet hub and the cannula hub are releasably coupled by a luer lock coupling.

11. The coaxial needle assembly according to claim 1 wherein the throw calibrator is infinitely adjustable between a minimum effective length and a maximum effective length, wherein the effective length is the distance between the distal end of the cannula and the insertion stop.

12. The coaxial needle assembly according to claim 1 wherein the throw calibrator comprises indicia that correspond to the throw distance of the biopsy device such that the indicia can be used to calibrate the coaxial needle assembly with the throw distance of a biopsy device.

13. A biopsy device system for the percutaneous removal of a specimen from an area of interest within a tissue mass, the biopsy device system comprising:
    a variable throw biopsy device having a needle assembly with an adjustable throw distance, the needle assembly comprising a biopsy cannula and a biopsy stylet which is received by the biopsy cannula in coaxially telescoping relationship and the throw distance comprising the distance the biopsy stylet travels relative to the biopsy cannula when the biopsy device is fired;
    a guide cannula defining a lumen configured to receive the needle assembly and having a proximal end and a distal end; and
    a throw calibrator adjustably carried by the guide cannula and having a biopsy device insertion stop configured to arrest the insertion of the needle assembly into a tissue mass by abutting a portion of the biopsy device against the insertion stop;
    wherein the throw calibrator may be used to adjust the position of the insertion stop relative to the guide cannula to calibrate the guide cannula with the throw distance of the biopsy device.

14. The biopsy device system according to claim 13 and further comprising a tip protector defining a lumen, wherein the tip protector is removably received on the guide cannula with the guide cannula extending through the lumen of the tip protector.

15. The biopsy device system according to claim 14 and further comprising at least one passageway for the flow of sterilization fluid between the tip protector and the guide cannula.

16. The biopsy device system according to claim 13 and further comprising a stylet removably received within the lumen and having a proximal end and a distal end, wherein the stylet and the guide cannula together form a coaxial needle assembly when the stylet is received within the lumen.

17. The biopsy device system according to claim 16 wherein the guide cannula further comprises a cannula hub attached to the proximal end of the cannula and the stylet further comprises a stylet hub attached to the proximal end of the stylet and the stylet hub is releasably coupled with the cannula hub.

18. The biopsy device system according to claim 13 wherein the position of the insertion stop relative to the distal end calibrates the effective length of the guide cannula with the throw distance of the biopsy device.

19. The biopsy device system according to claim 18 wherein the range of movement of the insertion stop relative to the cannula corresponds to the range of possible throw distances of the biopsy device.

* * * * *